(12) United States Patent
Josephson et al.

(10) Patent No.: US 9,097,644 B2
(45) Date of Patent: Aug. 4, 2015

(54) MAGNETIC RESONANCE-BASED VISCOMETERS AND METHODS

(75) Inventors: Lee Josephson, Reading, MA (US); Rui Hong, Tucson, AZ (US); Michael J. Cima, Winchester, MA (US); Ralph Weissleder, Peabody, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 1571 days.

(21) Appl. No.: 12/673,866

(22) PCT Filed: Aug. 15, 2008

(86) PCT No.: PCT/US2008/073346
§ 371 (c)(1),
(2), (4) Date: Feb. 8, 2011

(87) PCT Pub. No.: WO2009/026164
PCT Pub. Date: Feb. 26, 2009

(65) Prior Publication Data
US 2011/0124744 A1    May 26, 2011

Related U.S. Application Data

(60) Provisional application No. 60/965,218, filed on Aug. 17, 2007.

(51) Int. Cl.
*G01N 24/08* (2006.01)
*G01R 33/465* (2006.01)
(Continued)

(52) U.S. Cl.
CPC ............. *G01N 24/08* (2013.01); *G01R 33/465* (2013.01); *G01R 33/50* (2013.01); *G01N 27/745* (2013.01); *G01R 33/5601* (2013.01)

(58) Field of Classification Search
CPC ... G01N 24/08; G01N 27/745; G01N 24/081; G01N 24/10; G01N 24/082; G01R 33/46; G01R 33/448; G01R 33/5601; G01R 33/44; G01R 33/20; G01R 33/243; G01R 33/246; G01R 33/30; G01R 33/50; G01R 33/465
USPC ............ 73/54.41, 61.41, 61.43; 324/309, 307
See application file for complete search history.

(56) References Cited

U.S. PATENT DOCUMENTS

| 4,672,040 A | 6/1987 | Josephson |
| 5,136,095 A | 8/1992 | Tarnowski et al. |

(Continued)

FOREIGN PATENT DOCUMENTS

| WO | WO 90/06045 | 6/1990 |
| WO | WO 91/17428 | 11/1991 |

(Continued)

OTHER PUBLICATIONS

Fry, et al., "A new Approach to Template Purification for Sequencing Applications Using Paramagnetic Particles", *Research Report*, vol. 13, No. 1 (1992).

(Continued)

*Primary Examiner* — Hezron E Williams
*Assistant Examiner* — Marrit Eyassu
(74) *Attorney, Agent, or Firm* — Fish & Richardson P.C.

(57) ABSTRACT

This invention relates generally to magnetic resonance (MR)-based methods and kits for measuring the viscosity of liquid samples.

20 Claims, 5 Drawing Sheets

(51) Int. Cl.
    G01R 33/50    (2006.01)
    G01N 27/74    (2006.01)
    G01R 33/56    (2006.01)

(56) References Cited

U.S. PATENT DOCUMENTS

| | | | |
|---|---|---|---|
| 5,153,166 A | 10/1992 | Jain et al. | |
| 5,164,297 A | 11/1992 | Josephson et al. | |
| 5,254,460 A * | 10/1993 | Josephson et al. | 435/7.25 |
| 5,508,164 A | 4/1996 | Kausch et al. | |
| 5,512,439 A | 4/1996 | Hornes et al. | |
| 5,578,325 A | 11/1996 | Domb et al. | |
| 5,679,323 A | 10/1997 | Menz et al. | |
| 5,705,628 A | 1/1998 | Hawkins | |
| 5,801,003 A | 9/1998 | Shimamura et al. | |
| 5,858,534 A | 1/1999 | Sucholeiki | |
| 5,898,071 A | 4/1999 | Hawkins | |
| 5,973,138 A | 10/1999 | Collis | |
| 6,007,845 A | 12/1999 | Domb et al. | |
| 6,256,522 B1 | 7/2001 | Schultz | |
| 6,297,062 B1 | 10/2001 | Gombinski | |
| 6,346,813 B1 * | 2/2002 | Kleinberg | 324/303 |
| 6,361,944 B1 | 3/2002 | Mirkin et al. | |
| 6,509,059 B2 | 1/2003 | Yang et al. | |
| 6,751,491 B2 | 6/2004 | Lew et al. | |
| 7,357,016 B2 * | 4/2008 | Kurowski et al. | 73/54.41 |
| 2003/0092029 A1 | 5/2003 | Josephson et al. | |
| 2003/0174384 A1 | 9/2003 | Halas et al. | |
| 2004/0041562 A1 * | 3/2004 | Speier | 324/303 |
| 2006/0269965 A1 * | 11/2006 | Josephson et al. | 435/7.1 |
| 2007/0116602 A1 * | 5/2007 | Lee | 422/82.01 |
| 2008/0011977 A1 * | 1/2008 | Atwood | 252/62.51 R |
| 2009/0029392 A1 | 1/2009 | Josephson et al. | |
| 2009/0085557 A1 * | 4/2009 | Krozer et al. | 324/201 |
| 2013/0059293 A1 * | 3/2013 | Menon et al. | 435/5 |

FOREIGN PATENT DOCUMENTS

| | | |
|---|---|---|
| WO | WO 95/22963 | 8/1995 |
| WO | WO 96/09313 | 3/1996 |
| WO | WO 97/40181 | 10/1997 |
| WO | WO 98/04740 | 2/1998 |
| WO | WO 98/21587 | 5/1998 |
| WO | WO 01/00876 | 1/2001 |
| WO | WO 01/19405 | 3/2001 |
| WO | WO 02/098364 | 12/2002 |
| WO | WO 2005/061724 | 7/2005 |
| WO | WO2009/026164 | 2/2009 |
| WO | WO2009/026251 | 2/2009 |
| WO | WO2009/045551 | 4/2009 |

OTHER PUBLICATIONS

Gijs, "Magnetic bead handling on-chip: new opportunities for analytical applications," *Microfluid Nanofluid*, 1:22-40 (2004) XP002418117.

Hanaoka et al., "Selective sending of zinc ions with a novel magnetic resonance imaging contrast agent", *J. Chem. Soc. Perkin Trans*, 2001, vol. 2, pp. 1840-1843.

Högemann et al., "Improvement of MRI Probes to Allow Efficient Detection of Gene Expression", *Bioconjugate Chem.*, vol. 11, No. 6, pp. 941-946 (2000).

Högemann, et al.; "High throughput magnetic resonance imaging for evaluating targeted nanoparticle probes"; Bioconjugate Chem. 2002, 13, pp. 116-121.

International Search Report from corresponding PCT Application No. PCT/US2008/073515, ailed Nov. 17, 2008, 1 page.

Josephson et al., "High-Efficiency Intracellular Magnetic Labeling with Novel Superparamagnetic-Tat Peptide Conjugates", *Bioconjugate Chem*, vol. 10, No. 2, pp. 186-191 (1999).

Josephson et al., "Magnetic Nanosensors for the Detection of Oligonucleotide Sequences", *Angew. Chem. Int. Ed.*, vol. 40, No. 17, pp. 3204-3206 (2001).

Josephson, et al.; "The effects of iron oxides on proton relaxivity", Magn. Reson. Imagint 1988, vol. 6, pp. 647-653.

Kötitz et al., "Determination of the Binding Reaction Between Avidin and Biotin by Relaxation Measurements of Magnetic Nanoparticles," *J. Magnetism and Magnetic Materials*, 194:62-68 (1999).

Lewin et al., "Tat Peptide-derivatized magnetic nanoparticles allow in vivo tracking and recovery of progenitor cells", *Nature Biotechnology*, vol. 18, pp. 410-414 (Apr. 2000).

Niemeyer et al., "Self-Assembly of DNA-Streptavidin Nanostructures and Their Use as Reagents in Immuno-PCR,", *Nucleic Acid Research*, 27(23):4553-4561 (1999).

Notification Concerning Transmittal of International Preliminary Report on Patentability for corresponding PCT Application PCT/EP2008/073515, mailed Mar. 4, 2010, 2 pages.

Perez et al., "DNA-Based Magnetic Nanoparticle Assembly Acts as a Magnetic Relaxation Nanoswitch Allowing Screening of DNA-Cleaving Agents", *J. Am. Chem. Soc.*, vol. 124, No. 12, pp. 2856-2857, (2002)

Perez et al., "Magnetic relaxation switches capable of sensing molecular interactions," *Nature Biotechnology*, 20(8):816-820 (2002).

Perez et al., "Use of magnetic nanoparticles as nanosensors to probe for molecular interactions," *Chembiochem, Wiley-VCH Verlag*, 5(3):261-264 (2004).

Reynolds, et al.;"Method of determining nanoparticle core weight"; Anal. Chem. 2005, vol. 77, pp. 814-817.

Rogers et al., "Use of uspio-induced magnetic susceptibility artifacts to identify sentinel lymph nodes and lymphatic drainage patterns—1—Dependence of artifact size with subcutaneous Combidex® dose in rats," Magnetic Resonance Imaging, vol. 16, No. 8, pp. 917-923, 1998.

Sosnovik, et al.; "Emerging concepts in molecular MRI", Curr. Opin. Biotechnology 2007, 18:4-10.

Taketomi-Takahashi et al., "Magnetite ingested as a nutritional supplement: Unexpected source of MRI susceptibility artifact," American Journal of Roentgenology, vol. 188, pp. 1026-1027, 2007.

Tsourkas, et al.; "Magnetic relaxation switch immunosensors detect enantiomeric impurities"; Angew. Chem. Int. Ed. 2004, 43, pp. 2395-2399.

Whitesides, et al.; "Magentic separatins in biotechnology"; Trends in Biotechnology 1983; vol. 1; pp. 144-148.

Written Opinion for corresponding PCT Application PCT/EP2008/073515, mailed Nov. 17, 2008, 5 pages.

Zhao, et al.; "Magnetic sensors for protease assays"; Angew. Chem. Int. Ed. 2003, 42, pp. 1375-1378.

International Search Report and Written Opinion dated Nov. 7, 2008 from international application No. PCT/US2008/073346.

Rosencranz et al., "Clinical Laboratory Measurement of Serum, Plasma, and Blood Viscosity," Am J. Clin. Pathol., 125(Suppl 1): S78-S86 (2006).

Rosenson et al., "Distribution of blood viscosity values and biochemical correlates in healthy adults," Clinical Chemistry, 42:8, 1189-1195 (1996).

* cited by examiner

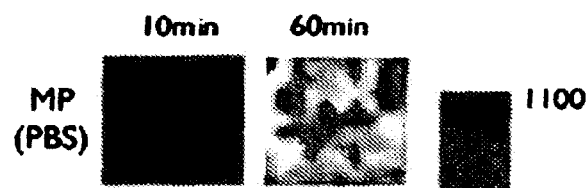
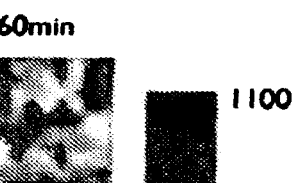
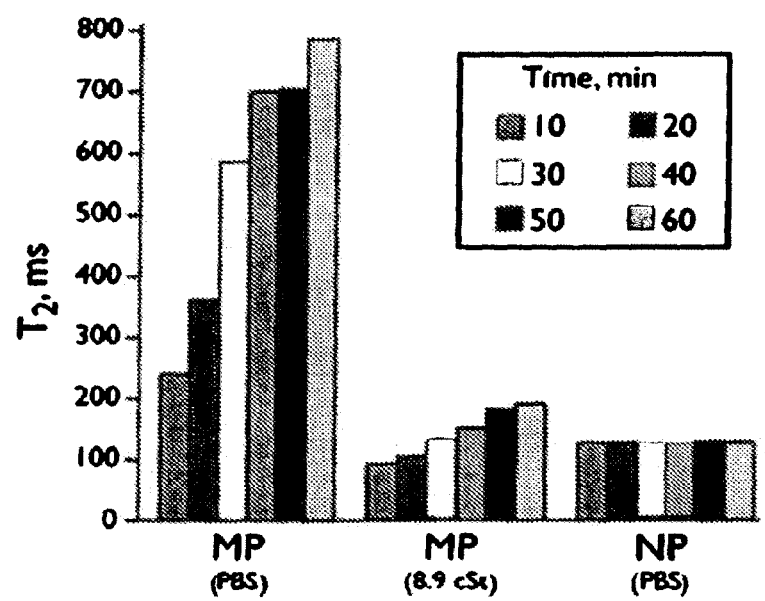
FIG. 3A FIG. 3B FIG. 3C FIG. 3D FIG. 3E FIG. 3F FIG. 3G thermal motion time remove field

MAGNETIC RESONANCE-BASED VISCOMETERS AND METHODS

This application is the national stage of International Application Number PCT/US2008/073346, filed on Aug. 15, 2008, which is based on and claims the benefit of the filing date of U.S. Provisional Application No. 60/965,218, filed on Aug. 17, 2007, all of which as filed are incorporated herein by reference in their entireties.

STATEMENT REGARDING FEDERALLY SPONSORED RESEARCH

This invention was made with Government support under Grant Numbers CA119349,EB000662,HL080731, and RB004626 awarded by the National Institutes of Health. The government has certain rights in the invention.

TECHNICAL FIELD

This invention relates generally to magnetic resonance (MR) based methods for measuring the viscosity of a liquid sample.

BACKGROUND

Viscosity is a measure of a liquid's resistance to flow. The viscosity of a liquid is typically measured using instruments known as viscometers, e.g., tube-type (capillary), falling body (timed fall), and rotational (drag torque) viscometers. See, e.g., Rosencranz, R. and Bogen, S. A. *Am. J. Clin. Pathol.* 2006, 125(Suppl 1): S78-S86.

SUMMARY

This invention relates generally to magnetic resonance (MR)-based methods for measuring the viscosity of liquids.

In one aspect, the invention features methods for determining the viscosity of a liquid, in which the liquid includes a solvent. The methods include: (i) exposing a sample that includes the liquid and two or more non-settling particles, each of the particles having a positive magnetic susceptibility, to an applied magnetic field, in which the applied magnetic field is of a strength sufficient to induce the particles to aggregate; and (ii) measuring a change in a nuclear relaxation property of the solvent caused by aggregation of the particles in the applied magnetic field.
The change in the nuclear relaxation property correlates with the viscosity of the liquid.

In another aspect, the invention features methods for diagnosing or monitoring the progress of hyperviscosity syndrome in a patient in need of such diagnosing or monitoring. The methods include: (i) obtaining a patient sample mixture including an aqueous sample from the patient, e.g., blood, serum, or plasma from the patient, and two or more non-settling particles, each of the particles having a positive magnetic susceptibility; (ii) exposing the patient sample mixture to an applied magnetic field, wherein the applied magnetic field is of a strength sufficient to induce the particles to aggregate; (iii) measuring a change in a nuclear relaxation property of water in the patient sample mixture caused by aggregation of the particles in the applied magnetic field; and (iv) determining viscosity of the blood, serum, or plasma on the basis of the change in the nuclear relaxation property of the water in the blood, serum, or plasma caused by aggregation of the particles in the applied magnetic field.

In a further aspect, the invention features kits for determining the viscosity of a liquid, e.g., an aqueous patient sample, in which the liquid includes a solvent. The kits include two or more non-settling particles, each of the particles having a positive magnetic susceptibility; and any one or more of the following: (i) two or more liquid standards of known viscosity; (ii) a standard curve (e.g., a hard copy or an electronic copy) or some other algorithm for determining viscosity, which is based on a plot of the rates of change in a nuclear relaxation property for two or more liquid standards of known viscosity against (1/known viscosity) for each of the standards; and optionally, (iii) a system or device capable of measuring (directly or indirectly) changes in a nuclear relaxation property of a solvent (e.g. a benchtop relaxometer); and optionally (iv) disposable containers for holding the particles and liquid (e.g., an NMR tube).

Embodiments can include one or more of the following features.

The nuclear relaxation property of the solvent can be the relaxation time of the solvent. The relaxation time can be $T_2$.

Step (ii) can include performing two or more measurements to determine the relaxation time of the solvent, in which at least two of the measurements are performed over a time interval when the sample is exposed to the applied magnetic field.

The methods can further include determining the rate of relaxation time change by: (a) calculating a difference between a relaxation time measured at about a start of the time interval and a relaxation time measured at about an end of the time interval; and (b) dividing the difference calculated in step (a) by about the duration of the time interval.

The methods can further include determining the viscosity of the liquid by locating the rate of relaxation time change for the sample on a plot of the rates of relaxation time change for two or more liquid standards of known viscosity against (1/known viscosity) for each of the standards.

In these methods, the solvent can be water or an organic solvent. In some embodiments, the organic solvent can include one hydrogen atom or two or more chemically equivalent hydrogen atoms.

The particles can be microparticles, such as superparamagnetic microparticles (e.g., the microparticles can include superparamagnetic metal oxide, such as iron oxide). The particles can have a buoyant density that is about the same as that of the solvent. The particles can further include polystyrene. The particles can have a magnetic moment of at least about $6 \times 10^{-12}$ emu (electromagnetic unit) per particle.

In certain embodiments, a hydrophilic or hydrophobic moiety can be covalently linked to the particles. For example, a carboxylic acid group can be covalently linked directly or indirectly to the particles.

In some embodiments, the volume of the sample can be from about 25 µL to about 500 µL, the applied magnetic field can be a homogenous magnetic field, and the strength of applied magnetic field can be about 0.47 T or about 1.5 T.

The methods can be performed using a benchtop magnetic resonance relaxometer and can be performed at a temperature of from about 20° C. to about 50° C.

The liquid can be selected from the group consisting of liquid foodstuffs, paints, coatings, drilling fluids, automotive oils, personal liquid hygiene products, and biological fluids. The liquid can have a viscosity of from about 3 cP to about 10 cP.

In various embodiments, the sample can be fully enveloped within a disposable container (e.g., an NMR tube), the time interval can be from about 2 minutes to about 60 minutes, and the aggregation of the particles in the sample is not discernible to the naked human eye.

The hyperviscosity syndrome can be the result of a disease or disorder associated with hyperviscosity syndrome. The disease or disorder associated with hyperviscosity syndrome can be polycythemia, Waldenström macroglobulinemia, multiple myeloma, or leukemia.

The methods can further include treating the disease or disorder associated with hyperviscosity syndrome by administering one or more therapeutic agents to the patient, wherein each of the therapeutic agents is administered in an amount effective to treat the disease or disorder associated with hyperviscosity syndrome.

As used herein, the term "non-settling" refers to particles having a relatively low tendency to settle by gravity during the course of the assay (i.e., particles that when in a collection, remain essentially suspended, as defined herein, in the liquid sample during the course of the assay). Candidate non-settling particles are evaluated using conventional light scattering techniques. A suspension containing the candidate particles and a solvent or a medium used to actually test the particles in later assays (total volume of 0.4 milliliters (mL)) is introduced into a 1 mL cuvette (the sample and cuvette volumes are chosen so as to create a relatively flat sample, thereby maximizing contact of the entire height of the sample with the light source). The cuvette is then placed in a light scattering machine (e.g., by Malvern Instruments, Southborough, Mass.), and the optical density of the suspension is monitored over a 2 hour period at room temperature. Particles that exhibit less than a 10% change in optical density are "non-settling" and thus suitable for use in the methods described herein.

As used herein, the phrase "the particles having a positive magnetic susceptibility" means that a magnetic field is strengthened by the presence of the particles. In different embodiments, the particles are paramagnetic, superparamagnetic, ferromagnetic, ferrimagnetic, or anti-ferromagnetic.

While not wishing to be bound by theory, it is believed that for particle aggregation to occur, the particles must exhibit attractive forces that can overcome the forces in the sample acting to keep the particles separated (e.g., Brownian motion and thermal agitation of the particles). As such, the particles used in the methods described herein generally have a high magnetic moment (as calculated on a per particle basis), at least about $6 \times 10^{-16}$ emu per particle (e.g., at least about $6 \times 10^{-15}$ emu per particle, at least about $6 \times 10^{-14}$ emu per particle, at least about $6 \times 10^{-13}$ emu per particle, at least about $6 \times 10^{-12}$ emu per particle, at least about $6 \times 10^{-11}$ emu per particle, or at least about $6 \times 10^{-10}$ emu per particle). Magnetic moments can be determined using a superconducting quantum interference device (SQUID) magnetometer (e.g., Quantum Design, San Diego, Calif.). Solutions of such particles typically exhibit time dependent $T_2$ (water proton spin-spin relaxation time) increases in the presence of a homogeneous magnetic field (see the Examples section).

As used herein, the term "solvent" means water and organic solvents in which the carbon skeleton is substituted directly or indirectly with one or more elements that have a naturally abundant, magnetically active isotope (i.e., an isotope having a nucleus with an odd-numbered mass). Examples of such elements and exemplary nuclei include, without limitation, hydrogen (e.g., $^1H$), boron ($^{11}B$), fluorine ($^{19}F$), and phosphorus ($^{31}P$).

Conventional symbols and units associated with viscosity are adhered to throughout this specification. The Greek symbol eta ($\eta$) refers to the International Union for Pure and Applied Chemistry (IUPAC) symbol for viscosity.

The Greek symbol mu ($\mu$) refers to the International Union for Pure and Applied Chemistry (IUPAC) symbol for dynamic viscosity. The SI physical unit of dynamic viscosity is the pascal-second (Pa·s), which is identical to 1 kg·m$^{-1}$·s$^{-1}$. The cgs physical unit for dynamic viscosity is the poise (P), which is typically expressed, particularly in ASTM standards, as centipoise (cP). The centipoise is sometimes used, because water has a viscosity of 1.0020 cP at 20° C. (1 P=1 g·cm$^{-1}$·s$^{-1}$). The relation between poise and Pascal-second is: 10 P=1 kg·m$^{-1}$·s$^{-1}$=1 Pa·s; and 1 cP=0.001 Pa·s=1 mPa·s.

The Greek symbol v refers to kinematic viscosity and is expressed in SI units as (m$^2$·s$^{-1}$). The cgs physical unit for kinematic viscosity is the stokes (abbreviated S or St). It is sometimes expressed in terms of centistokes (cS or cSt). In U.S. usage, stoke is sometimes used as the singular form (1 stoke=100 centistokes=1 cm$^2$·s$^{-1}$=0.0001 m$^2$·s$^{-1}$; 1 centistoke=1 mm$^2$/s).

Embodiments can include one or more of the following advantages.

The methods described herein can be practiced using a relatively small sample size. For the relaxometry measurements, a sample of 400 µL can be used, although samples as small as 50 µL have been used without a detectable loss of precision.

The methods described herein can be practiced using disposable glassware. The ability to avoid the cleaning and reuse of glassware can be advantageous for applications in, e.g., the clinical laboratory, in which biohazardous samples of human origin are routinely handled. For example, monitoring changes in the viscosity of blood or plasma (blood minus cells) is used in the diagnosis and management of diverse conditions as thrombogenic diseases, microcirculatory disorders, and sickle cell anemia. Although NMR tubes (e.g., from Norell) can be used, a number of less costly tubes compatible with relaxometers can also be used to provide $T_2$ measurements of identical values and reproducibility.

The methods described herein can be practiced using parallel or simultaneous processing of samples. We have employed an MR imager to measure time dependent changes in T2 on multiple samples simultaneously (see Examples section). Multiwell relaxometers, capable of measuring the T2 of a large number of samples simultaneously are also available.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference in their entirety.

Although methods and materials similar or equivalent to those described herein can be used in the practice of the present invention, preferred methods and materials are described below. The materials, methods, and examples are illustrative only and not intended to be limiting. Other features and advantages of the invention will be apparent from the detailed description and from the claims.

DESCRIPTION OF DRAWINGS

FIGS. 3A and 3B are representations of $T_2$ maps of the Example 1 microparticle solution in the absence of Triton X-100 at 10 minutes and 60 minutes, respectively, in a magnetic field (4.7 T, 25° C.).

FIGS. 3C and 3D are representations of $T_2$ maps of the Example 1 microparticle solution in the presence of Triton X-100 (solution viscosity=8.9 cSt) at 10 minutes and 60 minutes, respectively, in a magnetic field (4.7 T, 25° C.).

FIGS. 3E and 3F are representations of $T_2$ maps of the Example 1 nanoparticle solution at 10 minutes and 60 minutes, respectively, in a magnetic field (4.7 T, 25° C.).

FIG. 3G is a bar graph summarizing the T2 values of the wells shown in FIGS. 3A-3F at 10 minute intervals. A time dependent increase in $T_2$ occurred for the microparticles, but not for the nanoparticles. With a viscosity of 8.9 cSt, achieved by adding Triton X-100, a smaller increase in T2 occurred. T2 values represent mean values for the well.

DETAILED DESCRIPTION

Figure 1:
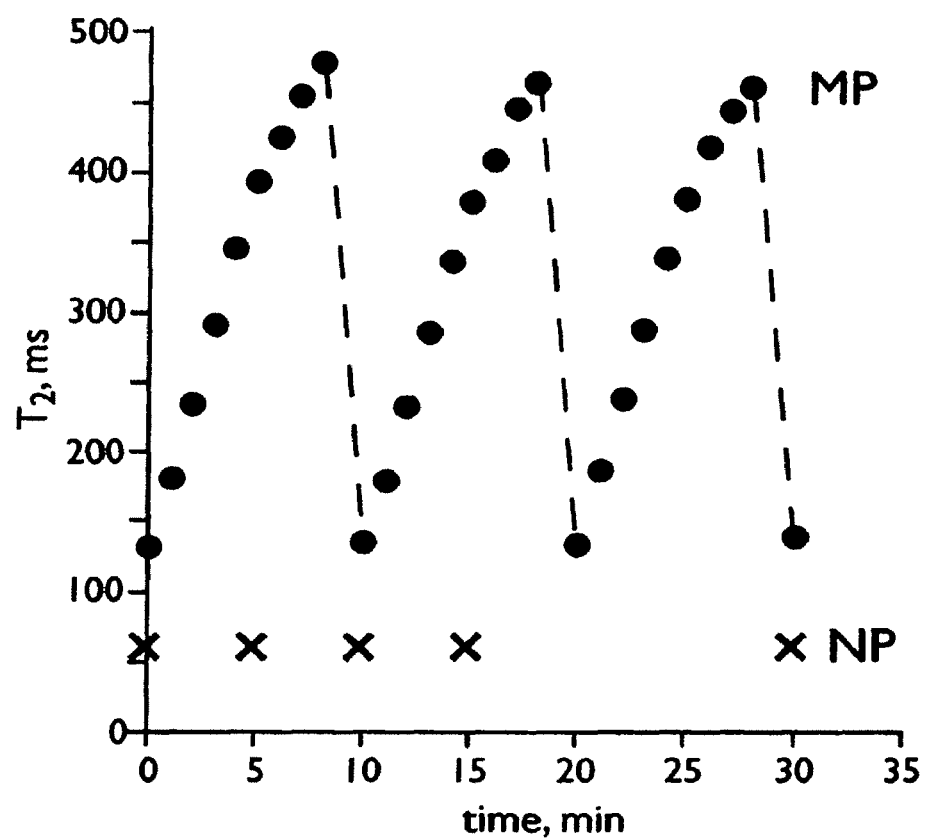
FIG. 1 is a graph showing the time dependence of $T_2$ in solutions containing microparticles (MP) and nanoparticles (NP) of Example 1 upon exposure to a homogeneous magnetic field in a relaxometer. $T_2$ of the Example 1 microparticle solution increased in the magnetic field (0.47 T) and returned to its original value when removed from the field. $T_2$ of the Example 1 nanoparticle was time independent. The dashed vertical lines shown on the graph indicate the time points at which the Example 1 microparticle solution was removed from the magnetic field.

This invention relates generally to magnetic resonance (MR)-based methods for measuring the viscosity of liquid samples.

This invention is based in part on the discovery that the magnetic field-induced aggregation of certain microparticles, as well as the associated $T_2$ increase, are reversible and slowed by increased solution viscosity. Solutions of non-settling, micron-sized, superparamagnetic microparticles were found to undergo a time dependent $T_2$ increase. This increase is believed to be caused by particle aggregation that occurs when the solutions are placed in homogenous magnetic fields. Particle aggregation is believed to result in the creation of large volumes of particle free solvent and heterogeneous $T_2$ values (as evidenced from MR imaging, see Examples section).

Additionally, a linear relationship was observed between the rate of $T_2$ change and the inverse of solution viscosity (j).

As such, the linear relationship between the rate in $T_2$ change and the reciprocal of viscosity can permit viscosity measurement by calibration of the system with a small number of standards, followed by determination of the viscosity of unknown solutions.

General Methodology

Data Collection

In some embodiments, the methods include:

(i) exposing a liquid sample that includes one or more solvents (e.g., one or two solvents) and two or more (e.g., a plurality of) non-settling, particles (e.g., microparticles), each of the particles having a positive magnetic susceptibility, to an applied magnetic field, in which the applied magnetic field is of a strength sufficient to induce the particles to aggregate;

(ii) measuring the change in a nuclear relaxation property of the solvent caused by aggregation of the particles in the applied magnetic field; and (iii) determining the viscosity of the sample from the rate of change in the nuclear relaxation property and a standard curve obtained from plotting the rates of change in a nuclear relaxation property for two or more liquid standards of known viscosity against (1/known viscosity) for each of the standards.

In general, any MR-based method that is capable of measuring (directly or indirectly) changes in a nuclear relaxation property of a solvent can be used in the methods described herein. Such methods can be MR imaging or MR non-imaging methods.

In some embodiments, the applied magnetic field can be, for example, about 0.47 Tesla (T), about 1.5 T, about 3 T, or about 9.4 T. Field strengths of about 0.47 T or 1.5 T are typically used. The applied magnetic field can be, but need not be, homogeneous, which is a requirement of magnets used to generate MR images. Selective excitation magnets were considered in early MR imager designs (see, e.g., Z. Abe, K. Tanaka, Y. Yamada, *Radiat Med* 2, 1-23). By way of example, a variable field strength hand-held magnet and excitation/receiver coil are used for analyzing the relaxation properties of samples within several millimeters of the magnet in commercial devices, see, e.g., the minispec ProFiler (Bruker Optics, Billerica, Mass.).

In some embodiments, the nuclear relaxation property of the solvent can be the relaxation time of the solvent (e.g., $T_2$).

Solvent, (e.g., water), spin-spin relaxation times ($T_2$) can be determined by relaxation measurements using a nuclear magnetic resonance benchtop relaxometer. In general, $T_2$ relaxation time measurements can be carried out at 0.47 T and 40° C. (e.g., using a minispec, Bruker Optics, Billerica, Mass.).

Alternatively, $T_2$ relaxation times can be determined by magnetic resonance imaging of 384-well plates (50 μL sample volume), allowing parallel measurements at higher throughput. In general, magnetic resonance imaging can be carried out using a 1.5 T superconducting magnet (Sigma 5.0; GE medical Systems, Milwaukee, Wis.) using $T_2$-weighted spin echo sequences with variable echo times (TE=25-1000 ms) and repetition times (TR) of 3,000 ms to cover the spectrum of the anticipated $T_2$ values. This technique is described in, for example, Perez, J. M., et al. *Nat Biotechnol* 2002, 20, 816-820; and Hogemann, D., et al. *Bioconjug Chem* 2002, 13, 116-121.

The extent of particle aggregation can also be determined without measurement of $T_2$ as delineated below:

1. Measurement of the $T_2^*$, or free induction decay, rather than $T_2$.

2. Measurement of the relaxation properties of a specific class of nucleus within the solvent (e.g., water protons) using an off-resonance radiation, i.e., radiation that is not precisely at the Larmour precession frequency.

3. Measurement of the height of a single echo obtained with a $T_2$ measuring pulse sequence rather than a complete echo train. Normal $T_2$ measurements utilize the declining height of a number of echoes to determine $T_2$.

4. Shifting the frequency or strength of the applied magnetic field, measuring the broadness of the proton absorption peak. Broader peaks or energy absorption are correlated with higher values of $T_2$.

Determination of Viscosity

As discussed above (and described in detail in the Examples sections), the inventors observed that there was a linear relationship between the rate of $T_2$ change and the inverse of solution viscosity (j).

The particle coagulation rate ($r_o$) of a rapid coagulation regime is described by:

$$r_o = 8\pi D_p a c^2_0 \quad [1]$$

where $D_p$ is the particle diffusivity, a is the particle radius, and $c_0$ is the initial particle concentration. The Stokes-Einstein relation provides that the particle diffusivity is given by:

$$D_p = kT/6\pi a \eta \quad [2]$$

where k is the Boltzmann constant, T is the temperature, and $\eta$ is the viscosity. Roch et al. showed that $T_2$ increases with aggregation in the large sphere limit such that $T_2$ is proportional to $\tau_D$, where:

$$\tau_D (= R^2_a / D_w) \quad [3]$$

is the time required for water's translational diffusion around a particle or an aggregate; $R_a$ is the radius of the agglomerate and $D_w$, is the diffusivity of water (Roch, A.; Gossuin, Y.; Muller, R. N.; Gillis, P. 1 *Magn. Magn. Mater.* 2005, 293, 532-539).

Shapiro et al. discussed the fact that the agglomerates are not densely packed (Shapiro, M. G.; Atanasijevic, T.; Faas, H.; Westmeyer, G. G.; Jasanoff, A. *Magn. Reson. Imaging* 2006, 24, 449-462). Indeed, they assume that the agglomerates are fractal so that the relationship between agglomerate size and number of particles within the agglomerate is given by $$R_a = n^{1/df} \quad [4]$$

where n is the number of particles in an agglomerate and df is the fractal dimension, which has values between 1.75 and 2.3. Thus, the combination of equations 3 and 4 suggests that $T_2$ is roughly linear with the number of particles within the aggregate. Further, examination of equations 1 and 2 shows that the rate of change of number of particles in an agglomerate will be inversely proportional to the viscosity of the medium. Equations 3 and 4 show that $\tau_D$, and thus $T_2$ in the large sphere limit, changes linearly with the number of the particles in the agglomerate if the fractal dimension is approximately 2. Thus, we expect the rate of $T_2$ change to be inversely proportional to the viscosity.

Measuring Changes in a Nuclear Relaxation Property of a Solvent

The inventions described herein, are based, in part, on the discovery that the magnetic field-induced aggregation of the microparticles, as well as the associated $T_2$ increase, are reversible and slowed by increased solution viscosity. Solutions of non-settling, micron-sized, superparamagnetic microparticles were observed to undergo a time dependent $T_2$ increase. This increase is believed to be caused by particle aggregation that occurs when the solutions are placed in homogenous magnetic fields. Particle aggregation is believed to result in the creation of large volumes of particle free solvent and heterogeneous $T_2$ values (as evidenced from MR imaging, see Examples section). A linear relationship was observed between the rate of $T_2$ change and the inverse of solution viscosity (j). As such, the linear relationship between the rate in $T_2$ change and the reciprocal of viscosity can permit viscosity measurement by calibration of the system with a small number of standards, followed by determination of the viscosity of unknown solutions.

Thus, in some embodiments, the methods can include:

A: performing two or more measurements to determine the relaxation time (e.g., $T_2$) of the solvent, wherein at least two of the measurements are performed over a time interval when the sample is exposed to the applied magnetic field; and/or B: determining the rate of relaxation time change by:

(a) calculating the difference between the relaxation time (e.g., $T_2$) measured at about a start of the time interval and the relaxation time measured at about an end of the time interval; and (b) dividing the difference calculated in step (a) by the duration of the time interval; and C: determining the viscosity of the liquid by locating the rate of relaxation time (e.g., $T_2$) change value for the sample on a plot of the rates of relaxation time change for two or more liquid standards of known viscosity against (1/known viscosity) for each of the standards. The viscosity of the standards can be determined using conventional methods (see, e.g., the Background and Examples section of this specification).

In various embodiments, the methods can include, e.g., A and C, B and C, or A, B, and C above.

The Liquid Sample

In general, the liquid can be any Newtonian or non-Newtonian naturally occurring or synthetic liquids that include one or more solvents (e.g., one or two solvents). Typically, the sample is in liquid state at room temperature, although samples that require temperatures greater than room temperature (e.g., 37° C. or 40° C.) to achieve the liquid state can also be assayed using the methods described herein. In general, any temperature that maintains the sample in the liquid state and is compatible with the device used to measure changes in a nuclear relaxation property can be used.

In some embodiments, the liquid sample can have a viscosity of from about 0.1 cP to about $10^9$ cP (e.g., from about 0.1 cP to about 25 cP, from about 3 cP to about 10 cP, from about 75 cP to about 125 cP, from about 750 cP to about 15,000 cP).

In some embodiments, a relatively small volume of liquid sample can be used in the methods described herein, e.g., from about 25 µL to about 500 µL. In embodiments, the sample volume can be about 50 µL, or about 400 µL.

Solvents

In general, the solvent can be water or any organic solvent in which the carbon skeleton is substituted directly or indirectly with one or more elements having a naturally abundant, magnetically active isotope. In some embodiments, the solvent can be a saturated, unsaturated, partially unsaturated, or aromatic hydrocarbon (i.e., a solvent that contains one or more protons, i.e., $^1H$). The solvent can be optionally substituted with one or more non-hydrogen substituents (e.g., halogen or hydroxyl). In certain embodiments, the organic solvent can include a single hydrogen atom as part of its structure (e.g., chloroform). In other embodiments, the organic solvent can include two or more hydrogen atoms and one or more sets of chemically equivalent hydrogen atoms. In various embodiments, the organic solvent can include in toto a single set of two or more chemically equivalent hydrogen atoms (e.g., methylene chloride or benzene).

In certain embodiments, the solvent can be a saturated, unsaturated, partially unsaturated, or aromatic fluorocarbon (e.g., hexafluorobenzene, perfluorokerosene (Fluorolube®), or fluorinated oligomers and polymers) that is optionally further substituted with one or more substituents.

Particles

In general, the particles that can be used in the methods described herein can be unfunctionalized, paramagnetic metals or metal oxides, such as superparamagnetic iron oxide. Metal oxides are sometimes preferred in applications where the particles are exposed to oxygen and water, or conditions under which metals in the 0 oxidation state are susceptible to oxidation. Metal oxide-based particles can further include other metals (e.g., cobalt, magnesium, or zinc) and/or other metal oxides (e.g., chromium dioxide).

The particles should generally have a magnetic moment (as calculated on a per particle basis) of at least about $6 \times 10^{-16}$ emu per particle. In certain embodiments, the particles can have a magnetic moment (as calculated on a per particle basis) of at least about $6 \times 10^{-12}$ emu per particle (e.g., at least about $6 \times 10^{-11}$ emu per particle or at least about $6 \times 10^{-10}$ emu per particle).

The particles should also have a relatively high $R_2$ relaxivity (as calculated on a per particle basis), e.g., of at least about $1 \times 10^8$ $s^{-1}$ per mM particle (e.g., at least about $1 \times 10^9$ $s^{-1}$ per mM particle or at least about $1 \times 10^{10}$ $s^{-1}$ per mM particle).

In certain embodiments, the particles can have a magnetic moment (as calculated on a per particle basis) of at least about $6 \times 10^{-12}$ emu per particle and an $R_2$ relaxivity (as calculated on a per particle basis), e.g., of at least about $1 \times 10^8$ $s^{-1}$ per mM particle.

In some embodiments, the particles can be microparticles having a particle size greater than about 100 nm to about 5 microns in diameter (e.g., from about 1 micron to about 5 microns). In other embodiments, the microparticles can have a particle size of about 1 micron. Such particles can be obtained, e.g., from commercial suppliers, which include DYNABEAD® magnetic microspheres from Invitrogen (Carlsbad, Calif.), microspheres from Bangs Laboratories (Fishers, Ind.), and ESTAPOR® Microspheres from Merck or EMD Life Sciences (Naperville, Ill.).

Smaller particles, such as nanoparticles having a particle size of from about 10 nm to about 100 nm, can be used provided that the nanoparticles meet the magnetic moment criteria described herein. This can be achieved, for example, by employing nanoparticles having a core containing a metal (s) instead of the corresponding metal oxide.

In some embodiments, the particles can be modified to include a coating (e.g., a polymeric coating, such as polystyrene or dextran) and/or one or more functional groups that are directly or indirectly attached to the particle (or to the particle coating if present). Such modifications can be used to adjust the buoyant density of the particle to match that of the solvent. In some instances, such a modification can further minimize the likelihood of particle settling. In other embodiments, such modifications can be used to facilitate dispersion of the particle in polar (e.g., water) and nonpolar (e.g., hydrocarbon) solvents. In embodiments, carboxylic acid-functionalized particles can be used to assay samples that contain water or polar protic and polar aprotic organic solvents. Carboxy functionalized particles can be obtained from commercial sources or prepared using conventional synthesis methods. For example, DYNABEADS® MyOne™-COOH magnetic microparticle can be obtained from Invitrogen.

Carboxy-functionalized particles can also be prepared using modifications of methods known in the art. For example, carboxy functionalized particles can be made according to the method of Gorman (see WO 00/61191). In this method, reduced carboxymethyl (CM) dextran is synthesized from commercial dextran. The CM-dextran and iron salts are mixed together and are then neutralized with ammonium hydroxide. As another example, carboxy-functionalized particles can also be made from polysaccharide coated particles by reaction with bromo or chloroacetic acid in strong base to attach carboxyl groups. As a further example, carboxy-functionalized particles can be made from amino-functionalized nanoparticles by converting amino to carboxy groups by the use of reagents such as succinic anhydride or maleic anhydride.

If desired, the carboxylic acid functional group can be further elaborated (e.g., converted to an amide) using conventional synthesis techniques. As another example, carboxy-functionalized particles can be converted to amino-functionalized particles by the use of water-soluble carbodiimides and diamines such as ethylene diamine or hexane diamine.

Dextran-coated particles can be made and cross-linked with epichlorohydrin. The addition of ammonia will react with epoxy groups to generate amine groups, see, e.g., Josephson et al., *Angewandte Chemie, International Edition* 40, 3204-3206 (2001); Hogemann et al., *Bioconjug. Chem.*, 2000, 11(6):941-6; and Josephson et al., "High-efficiency intracellular magnetic labeling with novel superparamagnetic-Tat peptide conjugates," *Bioconjug. Chem.*, 1999, 10(2):186-91.

In some embodiments, the so-called Ferrofluids (iron oxide hydrocarbon dispersions) can be used to assay samples that contain nonpolar solvents.

In some embodiments, a functional group can be linked indirectly to the particle (or a particle coating) via a linker. The linker can be chosen or designed primarily on factors such as convenience of synthesis, lack of steric hindrance, and biodegradation properties. Suitable linkers can include —O—, —S—, —SS—, —NH—, —NHC(O)—, —(O)CNH—, —NHC(O)($CH_2$)$_n$C(O)—, —(O)C($CH_2$)$_n$C(O)NH—, —NHC(O)($CH_2$)$_n$C(O)NH—, —C(O)O—, —OC(O)—, —NHNH—, —C(O)S—, —SC(O)—, —OC(O)($CH_2$)$_n$(O)—, —O($CH_2$)$_n$C(O)O—, —OC(O)($CH_2$)$_n$C(O)—, —C(O)($CH_2$)$_n$C(O)O—, —C(O)($CH_2$)$_n$C(O)—, —NH($CH_2$)$_n$C(O)—, —C(O)($CH_2$)$_n$NH—, —O($CH_2$)$_n$C(O)—, —C(O)($CH_2$)$_n$O—, —S($CH_2$)$_n$C(O)—, —C(O)($CH_2$)$_n$S—, —NH($CH_2$)$_n$—, —($CH_2$)$_n$NH—, —O($CH_2$)$_n$—, —($CH_2$)$_n$O—, —S($CH_2$)$_n$—, or —($CH_2$)$_n$S—, in which each n can be 1-100 (e.g., n can be 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, or 99). Linkers having cyclic, unsaturated, or cyclic unsaturated groups in place of the linear and fully saturated alkylene linker portion, ($CH_2$)$_n$, can also be used to attach the functional group to the particle.

In certain embodiments, the linker can be —NHC(O)($CH_2$)$_n$C(O)NH—, in which n can be 0-20. In certain embodiments, n can be 2, 3, 4, 5, or 6 (e.g., 2).

Applications

Liquid samples to be analyzed using the new methods described herein can include, without limitation, liquids that are used in industrial, household, or medical settings, such as liquid foodstuffs (e.g., honey, corn syrup, olive oil), lubricants, paints, coatings, drilling fluids, automotive fuels and fluids, liquid personal hygiene products (shampoos and liquid soaps), petroleum-based products (e.g., oils, tars, and pitch), and polymer solutions. The new methods and compositions can also be used to analyze biological fluids, such as blood, plasma, or serum.

These biological fluids can be analyzed to diagnose disorders, such as "hyperviscosity syndrome," which refers to an increase in blood, plasma, or serum viscosity and is associated with a variety of conditions and disorders, such as coronary and cerebrovascular disease, polycythemia, Waldenström macroglobulinemia, multiple myeloma, and leukemia (see, e.g., Rosenson, et al., *Clinical Chemistry* 1996, 42:8, 1189-1195 and Rosencranz and Bogen *Am. J. Clin. Pathol.* 2006, 125(Suppl 1):S78-S86). Symptoms can occur at a serum or plasma viscosity at or above 3 cP (Rosencranz and Bogen at S78).

Rosenson has demonstrated that normalized (taking into account the hematocrit and viscometer shear rate) whole blood (considered a non-Newtonian fluid—see Rosencranz and Bogen at S79) viscosity values correlate inversely with HDL cholesterol and positively with fibrinogen (Rosenson at 1189). Rosenson has also shown that plasma viscosity correlated with fibrinogen and serum viscosity correlated with total serum protein and LDL cholesterol (Rosenson at 1189).

The measurement of blood, plasma, and serum viscosity can therefore be used for diagnosing and monitoring hyperviscosity syndrome as well as for predicting the onset of or risk of having hyperviscosity syndrome and its associated disorders. Thus, in another aspect, this invention features methods for diagnosing or monitoring the progress of hyperviscosity syndrome in a patient in need of such diagnosing or monitoring. These methods include:

(i) exposing a sample comprising whole blood, plasma, or serum from the patient and two or more non-settling particles, each of the particles having a positive magnetic susceptibility, to an applied magnetic field, wherein the applied magnetic field is of a strength sufficient to induce the microparticles to aggregate;

(ii) measuring any change in a nuclear relaxation property of the water in the serum caused by aggregation of the particles in the applied magnetic field; and (iii) determining the viscosity of the sample on the basis of the change in a nuclear relaxation property of the water in the serum caused by aggregation of the particles in the applied magnetic field. Embodiments can include one or more of the features described herein.

In some embodiments, the methods can further include comparing the sample viscosity with reference values or with those obtained from a healthy subject to evaluate the hemorheological profile.

In some embodiments, the methods can further include treating the disease or disorder associated with hyperviscosity syndrome by administering one or more therapeutic agents to the patient, wherein each of the therapeutic agents is administered in an amount effective to treat the disease or disorder associated with hyperviscosity syndrome.

EXAMPLES

The invention is further illustrated by the following Examples. The Examples are provided for illustrative purposes only, and are not to be construed as limiting the scope or content of the invention in any way.

In the following examples, DYNABEADS® MyOne™-COOH magnetic microparticles, denoted as "MP" in the following examples were purchased from Invitrogen (Carlsbad, Calif.). The magnetic nanoparticle, denoted as NP, was the dextran coated MION-47 made as described in Josephson, L.; Tung, C. H.; Moore, A.; Weissleder, R. *Bioconjugate Chem.* 1999, 10, 186-191. All the other chemicals and solvents were purchased from Aldrich (St. Louis, Mo.). The value of 8000 Fe per NP was used (see Reynolds, F.; O'Loughlin, T.; Weissleder, R.; Josephson, L. *Anal. Chem.* 2005, 77, 814-817). The value of $2.8 \times 10^9$ Fe atoms per MP was determined from the manufacturer's number of particles per mL and the iron concentration. Particle settling refers to the percent change in the optical density at 405 nm at room temperature for 2 hours. All experiments were performed in phosphate buffered saline (PBS), pH 7.4, unless otherwise noted.

The particle sizes were measured on a ZETASIZER® 1000H5 light scattering instrument (Malvern Instruments, Southborough, Mass.). Relaxation times were measured on a relaxometer at 40° C., 0.47 T and 20 MHz (minispec mq20, Bruker Optics, Billerica, Mass.), and expressed in the unit of millisecond (ms). Magnetic moments (at 25° C.) were obtained on a superconducting quantum interference device (SQUID) magnetometer (Quantum Design, San Diego, Calif.). Phase contrast micrographs of MPs exposed to a magnetic field were obtained by diluting microparticles in unsolidified 0.5% agarose, and subjecting them to the magnetic field of the relaxometer in which the agar solidified. Agar was sectioned and observed with a Nikon® Eclipse E400™ microscope (Nikon Instruments Inc., Melville, N.Y.).

Viscosity was measured by using a cross-arm viscometer (Cole-Parmer, Vernon Hills, Ill.), and expressed in units of centistokes (cSt). To obtain MR images, 80 µL samples were placed in a section of a 384 well plate and spin echo images obtained at room temperature (TR=2000 msec, TE=40, 80, 120, 160 msec, FOV=4 cm, 256×256 matrix, slice thickness=1.5 mm) in a 4.7 T magnetic resonance system (Bruker BioSpin, Billerica, Mass.). Images were converted to T2 maps as described in Hogemann, D.; Ntziachristos, V.; Josephson, L.; Weissleder, R. *Bioconjugate Chem.* 2002, 13, 116-121.

Example 1

Initially, both a functionalized microparticle and a functionalized nanoparticle were evaluated for use in the methods described herein. The physical characteristics of the magnetic microparticle (MP), and magnetic nanoparticle (NP) are summarized in Table 1.

TABLE 1

| Particle | MP | NP |
|---|---|---|
| Size, nm | 1000 | 30 |
| Settling | <5.0% | None |
| $R_1$, $s^{-1}$ per mM Fe[a] | <1 | 18 |
| $R_2$, $s^{-1}$ per mM Fe[b] | 43 | 50 |
| M, emu per g Fe | 105 | 86.6 |
| Fe atoms per particle | $2.8 \times 10^9$ | 8,000 |
| $R_2$, mM particle[c] | $1.2 \times 10^{11}$ | 400,000 |
| M, emu per particle | $2.6 \times 10^{-11}$ | $6.2 \times 10^{-17}$ |

[a]$R_1$ and $R_2$ were measured at 0.47 T, 40° C.
[b]Magnetic moment at 5 T and 25° C.
[c]Relaxivities per particle are the relaxivities per mM Fe multiplied by the number of Fe atoms per MP or NP The MP is a microsphere, which includes superparamagnetic iron oxide crystals entrapped within a polystyrene matrix. The NP is a monodisperse crystal of superparamagnetic iron stabilized by a thick (10 nm) coating of T-10 dextran.

The MP and NP were quite different in size, 1000 nm and 30 nm in diameter respectively, although both were found to remain suspended for extended periods of time while in the presence of a gravitational field. It is believed that the NP remained suspended from Brownian motion or steric repulsion of the coating, since it is quite dense (both components of the NP, iron oxide and dextran, have densities greater than water: iron oxide density=5-6 g/cm$^3$ dextran density=1.17 g/cm$^3$). The larger MP remained suspended presumably because its buoyant density was similar to that of the media (polystyrene density varies with the type, but is generally between 1.0 and 1.1 g/cm$^3$).

The MP and NP had similar magnetic moments per gram of iron and similar $R_2$ relaxivities per mole of iron (s$^{-1}$mM$^{-1}$ as seen in Table 1. The NP had an $R_1$ of 18 s$^{-1}$ mM$^{-1}$, indicating that water was highly accessible to the surface of the iron oxide. In comparison, the MP had $R_1$ of less than 1 s$^{-1}$ mM$^{-1}$, indicating that the iron oxide crystals were shielded from water by the polystyrene matrix.

A second difference between the MP and the NP was apparent when the relaxivities and the magnetic moments were calculated on per particle basis. The MP had 2.8×10$^9$ Fe atoms per MP compared to 8000 Fe for the NP, i.e., there is 350,000 times more iron in the MP. Hence on a per particle rather than per iron basis, both the $R_2$ and the magnetic moment of the MP were far greater than those of the NP. For example, the magnetic moment of a single MP was about 4×10$^5$ times larger than that of a single NP.

Example 2

The spin-spin relaxation times ($T_2$) of the MP and NP solutions as a function of time were measured, and the data is summarized in the graph shown in FIG. 1. Solutions of MP or NP were added to 10 millimeter (mm) or 5 mm NMR tubes and incubated at 40° C. prior to making the $T_2$ measurements, which were obtained at 0.47 T and 40° C.

When the sample was placed in the 0.47 T field of the relaxometer, $T_2$ of the MP solution increased from 130 milliseconds (ms) to 400 ms in less than 6 minutes. The tube was removed from the relaxometer after a total of 8 minutes at 0.47 T, and the sample was incubated for 2 minutes at 40° C. in water bath (no agitation, no magnetic field). Withdrawal from the magnetic field produced a drop in $T_2$ to the original value of 130 ms, which again increased when placed in the relaxometer. Thus, solutions of MPs showed increasing $T_2$ values in the relaxometer, an increase which was readily reversed with short incubation outside of the magnetic field. In contrast, solutions of NPs exhibited completely time independent values of $T_2$ in the relaxometer. In fact, NP solutions exhibited relatively constant $T_2$s not only for 30 minutes (see FIG. 1), but for up to 24 hours (data not shown). Thus, solutions of MPs and NPs behaved differently in the relaxometer, with MPs undergoing $T_2$ increases, which were readily reversed by removing the sample from the magnetic field, while solutions of NPs gave time independent $T_2$ values.

Example 3

Figures 2A, 2B:
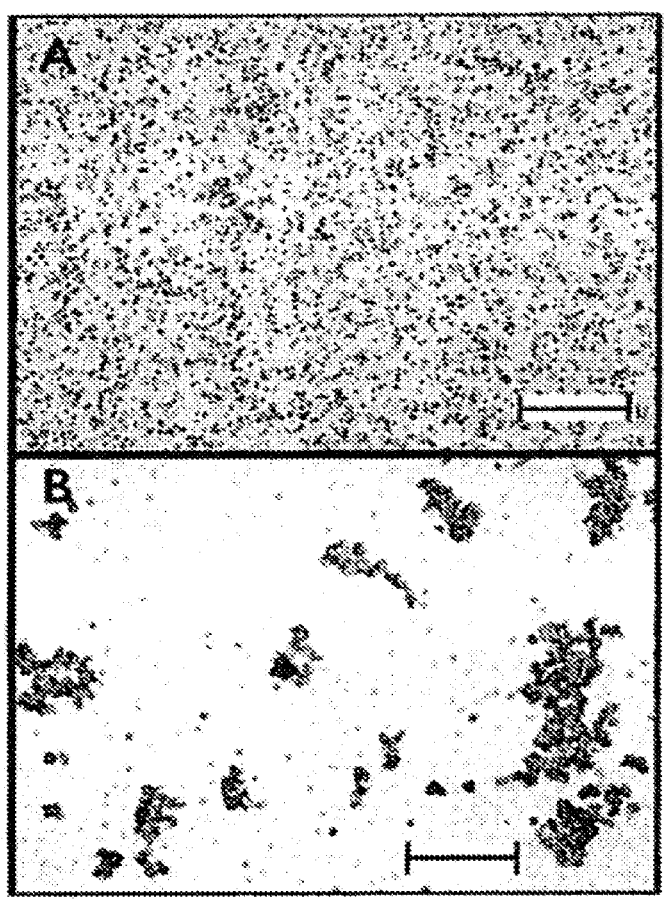
FIG. 2A is a representation of a micrograph of dispersed Example 1 microparticles immobilized in agar, which was allowed to solidify in the absence of a magnetic field.
FIG. 2B is a micrograph of Example 1 microparticles in agar, which was allowed to solidify in a magnetic field of 0.47 T. In both of FIGS. 2A and 2B, scale bars represent 50 microns.

To determine if placing MPs in the 0.47 T magnetic field altered their physical state, e.g., aggregated or dispersed, solutions of MPs were diluted into molten agar (0.5%) and allowed to gel either in the magnetic field at 40° C. or in a water bath at 40° C. After sectioning the solidified agar that contained the MPs, the distribution of MPs was examined by microscopy. When gelation occurred in the magnetic field, MP's existed as large aggregates, with large volume of solution completely lacking MPs (see FIG. 2A). In contrast, when agar gelation occurred in the water bath, MPs existed as dispersed, evenly distributed one micron microspheres (see FIG. 2B). Thus, the time dependent $T_2$ increase of MPs observed in the 0.47 T relaxometer was evidence of a magnetic field induced aggregation, resulting in the segregation of MPs into large aggregates leaving a large volume of solvent lacking in MPs.

Example 4

To determine if the MP aggregation and the time dependent $T_2$ increases were the result of the design of the relaxometer magnet or peculiarities of the sample tube, we examined the time dependent behavior of NPs and MPs in the 4.7 T magnet of an MR imager. Solutions of MPs and NPs were placed in the wells of a 384-well microtiter plate, and the $T_2$ weighted images were obtained at 10-minute intervals. As shown in FIGS. 3A and 3B, a time dependent $T_2$ increase was again observed for the MP solution with this magnet. In addition, after 60 minutes the $T_2$ of the MP solution in PBS became markedly heterogeneous, as would be expected by the development of large volumes of solution with no MPs (as observed in the micrograph shown in FIG. 2B). Because the formation of MP aggregates is believed to require MP movement, we reasoned that increasing media viscosity should retard the $T_2$ increase.

As shown in FIGS. 3C and 3D, when the viscosity of MPs in PBS increased to 8.9 cSt by the addition of Triton X-100, the time dependent increase in $T_2$ decreased. In contrast, the $T_2$ of NPs was time independent even in PBS (see FIGS. 3E and 3F). The time dependent increase of the average $T_2$s of wells shown in FIGS. 3A-3F was further investigated and shown in FIG. 3G. The MP solution showed a time dependent $T_2$ increase progressively over 60 minutes, an increase that was dramatically slowed by increased viscosity. On the other hand, the $T_2$ of the NP solution was completely time independent. These results are consistent with the particle clustering behavior observed in the 0.47 T magnetic field, thus suggesting the generality of the magnetic field induction in different fields.

Example 5

To further examine an implication of FIG. 3G, i.e., the magnetic field induced MP aggregation was slowed by increased medium viscosity, we examined whether $T_2$ changes might be used as a method to assay the viscosity of serum. Sera from patients suffering from multiple myeloma or Waldenström's macroglobulinemia typically exhibit increased viscosity, which is associated with severe lethargy, bleeding, headaches, vision problems, numbness and tingling in hands and feet but which can be corrected by aphoresis (see, e.g., Zarkovic, M.; Kwaan, H. C. *Semin. Thromb. Hemost.* 2003, 29, 535-542).

Figure 4A:
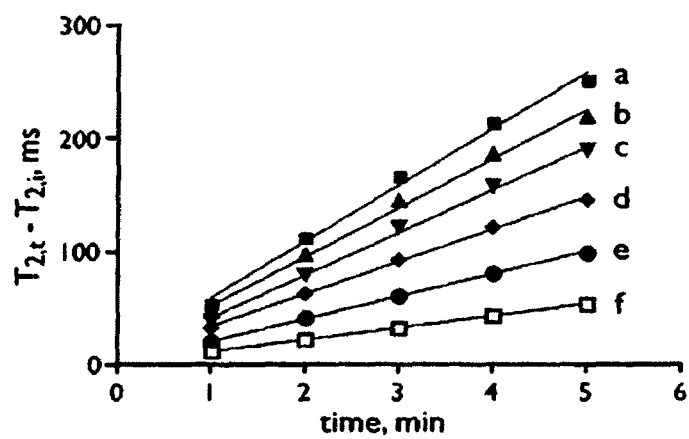
FIG. 4A is a graph showing changes in $T_2$ over time for synthetic myeloma serum at 0.47 T. $T_{2,i}$ is the initial or starting $T_2$. $T_{2,t}$ is the $T_2$ at some time t. The solutions were: a). FBS+20% PBS (v/v): b). FBS: c). FBS+10 mg/mL bovine IgG (v/w); d. FBS+20 mg/mL bovine IgG; e). FBS+50 mg/mL bovine IgG; and f). FBS+100 mg/mL bovine IgG.
Figure 4B:
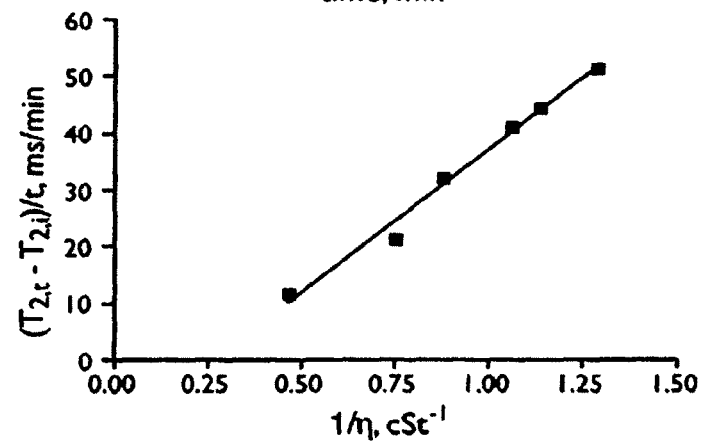
FIG. 4B is a graph showing the rate of $T_2$ change from (A) versus the reciprocal of viscosity.

Synthetic "myeloma sera" were created by the addition of bovine IgG to fetal bovine serum, to approximate the composition of real myeloma sera. Time dependent $T_2$ changes of MP suspension in the sera were determined in the relaxometer. As shown in FIG. 4A, the change in $T_2$ was linear with time, with the rate of $T_2$ change decreasing as serum viscosity increased. Importantly, a linear relationship was found between the rate of T2 change (see FIG. 4A) and the inverse of solution viscosity (j) as shown in FIG. 4B. The linear relaxation between the rate in $T_2$ change and the reciprocal of viscosity permits viscosity measurement by calibration of the system with a small number of standards, followed by determination of the viscosity of unknown solutions.

Figure 5A:
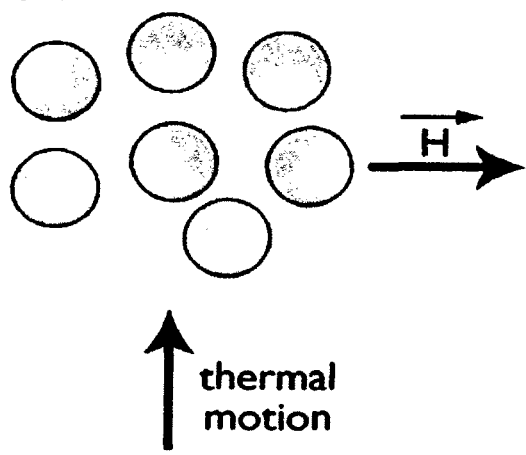
FIGS. 5A-5D are schematic representations of the reversible magnetic field induced aggregation of MPs. When dispersed MPs (FIG. 5A) are placed in a magnetic field, MPs become magnetic and all magnet moments are aligned with the field (FIG. 5B). Over time, when two MPs come close together, they form aggregates, which are effectively a small number of larger magnets (FIG. 5C). When the field is removed, MPs demagnetize (FIG. 5D). Lacking aligned magnetic moments, MPs aggregates return to the dispersed state (FIG. 5A).
Figure 5B:
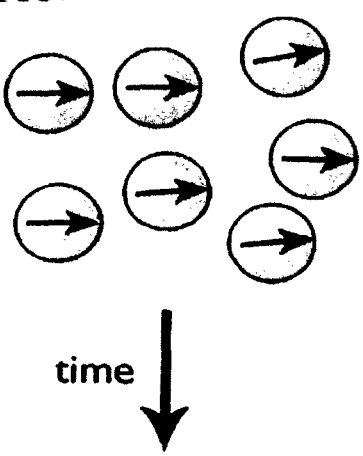
Figure 5D:
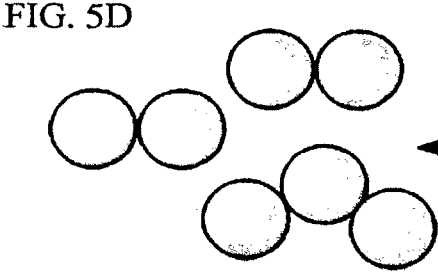
Figure 5C:
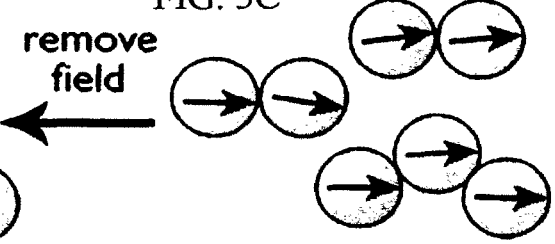

Micrographs of the high and low $T_2$ states (FIGS. 2A and 2B), and the effects of viscosity on retarding $T_2$ changes (FIGS. 3C and 3D and 4A and 4B), lead to the model of magnetic field induced MP aggregation shown in FIGS. 5A-5D. As shown in FIG. 5A, in the absence of an applied magnetic field, MPs are non-magnetic due to the superparamagnetic nature of the iron oxide. With the application of a homogeneous magnetic field, the MPs become magnetic and the magnetic moments of MPs align with the applied magnetic field (see FIG. 5B). When MPs move into close proximity by diffusion, aggregation occurs because magnetic coupling (magnetic attraction between MP's) results (FIG. 5C). With the removal of the MP aggregates from the external magnetic fields, the Neel relaxation of superparamagnetic iron oxide crystals eliminates magnetic coupling, and thermal forces return the MPs to a dispersed state (FIG. 5D).

The model is supported by estimates of the strength of magnetic dipolar coupling employ the parameter, $\lambda$, a dimensionless number used to evaluate the stabilization of magnetic coupling relative to thermal motion (Klokkenburg, M.; Vonk, C.; Claesson, E. M.; Meeldijk, J. D.; Erne, B. H.; Philipse, A. P. 1 *Am. Chem. Soc.* 2004, 126, 16706-16707). Here, $\lambda = \mu_0 \mu^2 / (4\pi k_\beta T d^3)$. where $\mu_0$ is the permeability of vacuum, $\mu$ the magnetic moment of one particle, and d the diameter of the particle. For values of $\lambda$ greater than 2, magnetic coupling is typically strong enough to overcome thermal motion. From the magnetic moments obtained (see Table 1), $\lambda$ of the MP is about $1.8 \times 10^4$ compared to that of the NP which is $3.6 \times 10^3$. Thus the MP aggregation and the increasing $T_2s$ of MPs exhibited in homogeneous magnetic fields were the result of the large magnetic moment per particle, which lead to stabilized MP aggregation, while the smaller magnetic moment of NPs yielded magnetic coupling is not strong enough to overcome thermal randomization or permit aggregate formation.

The magnetic field induced aggregation of MPs described here results in T2 increases, while the ligand clustering of NPs results in a $T_2$ decrease. Models developed to describe the effect of the size of magnetic spheres on $T_2$ employ two parameters: $\tau_d$ the diffusion time for water, and $\Delta\omega$, the difference in angular frequency between the local field experienced by a proton at the equatorial line of the particle or cluster surface and in the bulk (see, e.g., Muller, R. N.; Gillis, P.; Moiny, F.; Roch, A. *Magn. Reson. Med.* 1991, 22, 178-182; Gillis, P.; Koenig, S. H. *Magn. Reson. Med.* 1987, 5, 323-345; Brooks, R. A.; Moiny, F.; Gillis, P. *Magn. Reson. Med.* 2001, 45, 1014-20; Yung, K. T. *Magn. Reson. Imaging* 2003, 21, 451-463; Roch, A.; Gossuin, Y.; Muller, R. N.; Gillis, P. 1 *Magn. Magn. Mater.* 2005, 293, 532-539; and Shapiro, M. G.; Atanasijevic, T.; Faas, H.; Westmeyer, G. G.; Jasanoff, A. *Magn. Reson. Imaging* 2006, 24, 449-462).

An increase in $T_2$ is expected to occur with size increase (aggregate formation) when $\Delta\omega\tau_d > 1$, which is believed to be the case for MP here. The MP aggregation leads to large volumes of solvent without aggregates as was evident by microscopy (FIGS. 2A and 2B), and two phases of restricted water diffusion, i.e., the heterogeneous pattern of $T_2s$ seen by MRI (FIGS. 3A-3D). The increase in the average solution $T_2$ is therefore likely due to the large fraction of solution that is particle free.

On the other hand, for NPs, the motional averaging condition is fulfilled ($\Delta\omega\tau_d < 1$). NP clustering decreases $T_2$, because NP clustering results in a smaller number of larger magnetic field inhomogeneities into which all water molecules can diffuse. MR images of solutions of NPs (FIGS. 3E and 3F) are therefore homogeneous (Perez, J. M.; Josephson, L.; Hogemann, D.; Weissleder, R. *Nat. Biotechnol.* 2002, 20, 816-820; Tsourkas, A.; Hofstetter, O.; Hofstetter, H.; Weissleder, R.; Josephson, L. *Angew. Chem., Int. Ed.* 2004, 43, 2395-2399; and Zhao, M.; Josephson, L.; Tang, Y.; Weissleder, R., Magnetic sensors for protease assays. *Angew. Chem., Int. Ed.* 2003, 42, 1375-1378) and the $T_2s$ are time independent because the field is not strong enough to induce aggregation.

OTHER EMBODIMENTS

A number of embodiments of the invention have been described. Nevertheless, it will be understood that various modifications may be made without departing from the spirit and scope of the invention.

What is claimed is:

1. A method for determining viscosity of a liquid, wherein the liquid comprises a solvent, the method comprising:
   (i) exposing a sample comprising the liquid and two or more non-settling particles, each of the particles having a positive magnetic susceptibility and a magnetic moment of at least about $6 \times 10^{-16}$ emu per particle, to an applied magnetic field, wherein the applied magnetic field is of a strength sufficient to induce the particles to aggregate; and
   (ii) measuring a change in a nuclear relaxation property of the solvent caused by aggregation of the particles in the applied magnetic field;
   wherein a change in the nuclear relaxation property relates to the viscosity of the liquid.

2. The method of claim 1, wherein the nuclear relaxation property of the solvent is a relaxation time of the solvent.

3. The method of claim 2, wherein step (ii) comprises performing two or more measurements to determine the relaxation time of the solvent, wherein at least two of the measurements are performed over a time interval when the sample is exposed to the applied magnetic field.

4. The method of claim 3, wherein the method further comprises determining a rate of relaxation time change by:
   (a) calculating a difference between a relaxation time measured at a start of the time interval and a relaxation time measured at an end of the time interval; and
   (b) dividing the difference calculated in step (a) by a duration of the time interval.

5. The method of claim 4, wherein the method further comprises determining the viscosity of the liquid by locating the rate of relaxation time change for the sample on a plot of rates of relaxation time change versus 1/viscosity for two or more liquid standards, wherein viscosity for each standard is known.

6. The method of claim 2, wherein the relaxation time is T2.

7. The method of claim 1, wherein the solvent is water.

8. The method of claim 1, wherein the solvent is an organic solvent.

9. The method of claim 1, wherein the particle is a microparticle having a size greater than 100 nanometers to about 5 microns.

10. The method of claim 9, wherein the microparticle is a superparamagnetic microparticle.

11. The method of claim 10, wherein the microparticle comprises a superparamagnetic metal oxide.

12. The method of claim 9, wherein the microparticles have an R2 relaxivity of at least about $1 \times 10^8$ $s^{-1}$ per mM particle.

13. The method of claim 9, wherein the microparticles have a magnetic moment of at least about $6 \times 10^{-12}$ emu per particle.

14. The method of claim 9, wherein the microparticles have a size of from 1 to 5 microns.

15. The method of claim 14, wherein the microparticles have a magnetic moment of at least about $6 \times 10^{-12}$ emu per particle.

16. The method of claim 1, wherein the particle has a buoyant density that is about the same as that of the solvent.

17. The method of claim 16, wherein the nanoparticles have an R2 relaxivity of at least about $1 \times 10^8$ $s^{-1}$ per mM particle.

18. The method of claim 1, wherein a hydrophilic or hydrophobic moiety is covalently linked to the particle.

19. The method of claim 1, wherein a carboxylic acid group is covalently linked directly or indirectly to the particle.

20. The method of claim 1, wherein the particles have an R2 relaxivity of at least about $1 \times 10^8$ $s^{-1}$ per mM particle.

* * * * *

UNITED STATES PATENT AND TRADEMARK OFFICE
CERTIFICATE OF CORRECTION

PATENT NO. : 9,097,644 B2  
APPLICATION NO. : 12/673866  
DATED : August 4, 2015  
INVENTOR(S) : Josephson et al.

Page 1 of 1

It is certified that error appears in the above-identified patent and that said Letters Patent is hereby corrected as shown below:

In the specification

Column 1, line 15, delete "CA119349,EB000662,HL080731," and insert -- CA119349, EB000662, HL080731, --;

In the claims

Column 16, line 46, Claim 6, delete "T2." and insert -- $T_2$. --.

Signed and Sealed this
Twenty-second Day of March, 2016

Michelle K. Lee
*Director of the United States Patent and Trademark Office*